(12) United States Patent
Bray et al.

(10) Patent No.: US 8,303,551 B2
(45) Date of Patent: Nov. 6, 2012

(54) WOUND DRESSINGS

(75) Inventors: Roger Bray, Nuneaton (GB); Champa Patel, Coventry (GB); Philip Roy Caskey, Cambridge (NZ)

(73) Assignees: Convatec Limited, Flintshire (GB); Apimed Medical Honey Limited, Cambridge (NZ)

( * ) Notice: Subject to any disclaimer, the term of this patent is extended or adjusted under 35 U.S.C. 154(b) by 572 days.

(21) Appl. No.: 12/108,421

(22) Filed: Apr. 23, 2008

(65) Prior Publication Data
US 2009/0012440 A1    Jan. 8, 2009

Related U.S. Application Data

(63) Continuation of application No. 10/497,445, filed on Oct. 4, 2004, now abandoned.

(30) Foreign Application Priority Data

Dec. 3, 2001    (GB) .................................. 0128936.2

(51) Int. Cl.
*A61F 13/00*    (2006.01)

(52) U.S. Cl. .......................................... 604/304; 602/48
(58) Field of Classification Search .................. 604/304, 604/306; 602/48, 41–43; 424/70.06, 447
See application file for complete search history.

(56) References Cited

U.S. PATENT DOCUMENTS

| | | |
|---|---|---|
| 6,956,144 B2 | 10/2005 | Molan |
| 2009/0012440 A1 | 1/2009 | Bray et al. |

FOREIGN PATENT DOCUMENTS

| | | |
|---|---|---|
| WO | WO 00/09176 | 2/2000 |
| WO | WO 01/41776 A2 | 6/2001 |
| WO | WO 02/00269 A1 | 1/2002 |
| WO | WO 02/087644 A1 | 11/2002 |

OTHER PUBLICATIONS

P.C. Molan et al., "The Effect of Gamma-Irradiation on the Antibacterial Activity of Honey", Journal of Pharmacy and Pharmacology, London, GB, vol. 48, No. 11, pp. 1206-1209, Nov. 1996.

*Primary Examiner* — Michele M Kidwell
(74) *Attorney, Agent, or Firm* — Sughrue Mion, PLLC

(57) ABSTRACT

A wound dressing comprises a wound-contacting layer composed of a mixture of honey and a moisture-absorbing agent; a water-permeable fabric backing layer; and an intermediate layer comprising water-permeable fabric impregnated with a mixture of honey and a moisture-absorbing agent.

14 Claims, 1 Drawing Sheet

WOUND DRESSINGS

This is a continuation of application Ser. No. 10/497,445 filed Oct. 4, 2004 now abandoned. The entire disclosure(s) of the prior application(s), application number(s) Ser. No. 10/497,445 is considered part of the disclosure of the accompanying continuation application and is hereby incorporated by reference.

FIELD OF THE INVENTION

This invention relates to wound dressings containing honey.

It has been long known that honey possesses antimicrobial properties that make it suitable for use in treating a range of infections and skin disorders. This antimicrobial activity can be attributed to a number of factors, in particular the natural presence in honey of hydrogen peroxide ($H_2O_2$), its high saccharide content (which tends to dehydrate bacteria by osmosis) and its relative acidity (normally around pH 4). Additionally, those honeys produced by bees that have fed on nectar from manuka blossom possess enhanced antimicrobial potency, due to the presence in such honeys of an as yet unidentified substance known simply as "unique manuka factor" (UMF).

The antimicrobial properties possessed by all honeys (and particularly those containing UMF) also render honey suitable for use in the dressing of wounds, where it assists in preventing infection, the debridement of necrotic tissue, the deodorising of malodorous wounds and the minimisation of scar formation. However, an obvious problem associated with the use of honey in such circumstances is that it is a rather runny substance, with the result that the use of natural honey in a wound dressing is messy and impractical and the wound dressing has no absorbing capacity, so that on an exuding wound it rapidly becomes unevenly liquefied and runs off the wound. This also causes dilution of the antimicrobial effect.

BACKGROUND ART

Attempts have been made in the past to overcome this problem by combining honey with viscosity-enhancing additives. Several such formulations are mentioned in WO 01/41776. WO 00/09176 discloses a wound treatment composition comprising an adsorbent material for adsorbing moisture on or around a wound and a saccharide or polysaccharide or derivative thereof. WO 02/00269 (published on $3_{rd}$ Jan. 2002) also discloses a wound dressing comprising a honey composition and a base material and optionally further layers for adhesion.

DISCLOSURE OF THE INVENTION

We have carried out experimental work that has confirmed that it is possible to create a sheet of dimensionally stable flexible non-sticky material by combining honey with a moisture-absorbing agent (such as sodium alginate powder) and allowing the mixture to set. When sheets of such material were subjected to a "Paddington Cup test" (as described in the 1996 Addendum to the British Pharmacopoeia, p1943), in which a saline solution is applied to the upper surface of a sample sheet clamped between a pair of flanges, it was found that the material readily breaks down and that saline passes through the sheet in less than 24 hours. Saline liquid also passes through a fabric layer in the same test in less than 24 hours. It has further been found that a fabric impregnated with pure honey is liquid water-permeable. Most surprisingly in view of these findings, however, it was discovered that a three-layer structure in which a honey-containing sheet of the type mentioned above is supported by a water-permeable fabric backing layer, with an intermediate layer of fabric impregnated with the honey mixture, can be substantially impervious to liquid water and aqueous saline liquid. Moreover, such substantially liquid-impervious composite material still has a significant liquid-absorption capacity, together with a high degree of permeability to water vapour generally, being capable of achieving a 24-hour moisture-vapour transmission rate of at least 20 g per 100 $cm^2$ and a 24-hour total fluid handling capacity of at least 35 g per 100 $cm^2$.

In the context of this invention, the term "impervious" is used in relation to the composite structure in the sense that liquid water (or an aqueous liquid such as saline solution) does not penetrate all the way through the structure and emerge in the liquid phase at the opposite face. The above-mentioned "Paddington Cup test" can serve as a test for this purpose, a composite being considered impervious if the liquid saline does not pass through it within 24 hours under that test.

The composite material is therefore ideally suited for use as a moist wound dressing, which assists in the healing of exuding wounds, since it retains its structural integrity in moist conditions, is able to form a barrier to liquid water, and yet both absorbs liquid water and transmits substantial amounts of water vapour at a steady rate. Both liquid absorbency and vapour transmission can be important. Absorbed liquid will include other wound fluid components and wound debris, as well as water. Moisture vapour transmission is an on-going property of the dressing whereas liquid absorption (absorbency) is a property which attains a maximum level.

The invention therefore provides, in one aspect, a wound dressing comprising: a wound-contacting layer composed of a mixture of honey and a moisture-absorbing agent; a water-permeable fabric backing layer; and an intermediate layer comprising water-permeable fabric impregnated with a mixture of honey and a moisture-absorbing agent. The wound dressings of the invention preferably are substantially impervious to liquid water but permeable to water vapour as manufactured, preferably even after sterilisation.

Generally speaking the wound-contacting and intermediate layer are in direct physical contact as are the intermediate layer and backing layer, although liquid and vapour contact is sufficient.

To provide structural integrity and strength, the honey mixture in the wound-contacting and intermediate layers preferably forms a continuum, as does the fabric in the backing and intermediate layers. In other words, the wound-contacting layer and the intermediate layer preferably form a first continuous phase and the fabric layer and intermediate layer preferably form a second continuous phase, the first and second continuous phases overlapping to form the intermediate layer. This may be achieved, for example, by spreading the honey mixture over a layer of fabric and allowing the mixture only partially to impregnate the fabric before it sets. This structural integrity also assists in removal of a used dressing in one piece.

The invention therefore provides, in another aspect, a method of manufacturing a wound dressing, comprising the steps of: providing a layer of a water-permeable fabric material; providing a mixture of honey and a moisture-absorbing agent; spreading said mixture over said fabric layer; allowing a portion of said mixture to impregnate an upper sub-layer of said fabric layer; and allowing said mixture to set; thereby producing a dressing comprising a wound-contacting layer composed of a mixture of honey and a moisture-absorbing agent, a water-permeable fabric backing layer, and an intermediate layer comprising fabric impregnated with said mixture of honey and moisture-absorbing agent.

In preferred embodiments, the three-layer structure is well defined, with the wound-contacting layer being free (or substantially free) from fibres such as fabric fibres from the backing layer and the fabric backing layer being free (or substantially free) from honey. The thickness of the intermediate layer e.g. as formed by partial impregnation of the fabric backing layer by the honey mixture may, for example, be from 100 µm to 1,000 µm, preferably from 200 to 500 µm.

Preferably, the honey layer forms a substantially homogeneous solid phase gel sheet. To ensure this, the ratio of honey to moisture-absorbing agent in the wound-contacting layer needs to be controlled within certain limits. Generally, the weight ratio of moisture-absorbing agent to honey should be within the range from 1:2 or 1:3 to 1:14 and preferably in the range from 1:2 or 1:3 or 1:4 to 1:10.

The preferred ratio of moisture-absorbing agent to honey has been found to be affected by irradiation, which is the preferred method for sterilising the wound dressings of the invention after manufacture and prior to use. Either gamma-irradiation or electron-beam irradiation can be used. The dressing can be irradiated by 25 kGy or more, or by lower amounts sufficient to achieve sterilisation. Surprisingly, it has been found that the ability of the honey layer to absorb liquid is diminished substantially and to a similar degree by both gamma-irradiation and electron-beam irradiation, if the ratio of moisture-absorbing agent to honey is very low, i.e. in compositions containing a relatively low proportion of moisture-absorbing agent. To ensure that the composite material retains its optimal properties, that is to say it is substantially impervious to liquid water but permeable to water vapour and with good liquid absorbency, even after irradiation, it is preferred that the weight ratio of moisture-absorbing agent to honey is in the range from 1:2 or 1:3 or 1:4 to 1:5. In preferred embodiments, the liquid absorbency is at least 15 g per 100 $cm^2$ after irradiation.

The identity of the moisture-absorbing agent and its molecular weight will also affect the constitution of the honey mix, and the precise identity and molecular weight of the agent used for best results may easily be determined by experiment. The moisture-absorbing agent may be selected from those which are non-toxic and pharmaceutically acceptable. Suitable moisture-absorbing agents include alginate salts such as sodium alginate (e.g. Keltone™ HVCR sodium alginate) and modified cellulose polymers such as carboxymethylcellulose (CMC), generally in powder form.

The water-permeable fabric for the intermediate and backing layers is preferably a needled non-woven fabric, but woven fabric may also be used. It is preferably a calcium alginate fabric, but other fabric materials such as carboxymethylcellulose or polyester may be used. As mentioned above, the same fabric is preferably used for both layers. The fabric density is preferably in the range 100 to 200, for example 150 to 180 gsm ($gm^{-2}$), although use of a lighter or heavier fabric may be possible. However, with lighter weight fabrics, for example of 70 gsm or less, it may be more difficult to produce dressings substantially impervious to liquid.

The amount of the mixture of honey and water-absorbing agent applied to the water-permeable fabric is desirably in the range 1000 to 5000 gsm ($gm^{-2}$), preferably 1500 to 4500 gsm, more preferably 2200 to 4200 gsm, although lower or higher amounts may be used. When the amount of the mixture is substantially below 1500 gsm, for example down to 1350 gsm or less, the dressings may not be substantially impervious to liquid.

A particularly preferred dressing is composed of non-woven calcium alginate fabric of 130-170 gsm, preferably about 150 gsm, impregnated with 2000-3000 gsm, preferably about 2500 gsm, of a mixture of sodium alginate and honey in a ratio by weight of 1:3 to 1:5, preferably about 1:4, so as to form a wound-contacting layer of the sodium alginate/honey mixture, an intermediate layer of the fabric impregnated with the sodium alginate/honey mixture and a backing layer of the fabric.

The dressings may also include one or more active pharmaceutical components to augment or supplement the properties of the dressing, particularly those components whose activity supplements those of honey, so that the wound-contacting layer need not be composed solely of honey and the moisture-absorbing agent. For example, an antimicrobial agent, or an antibiotic, or an anaesthetic, or an anti-inflammatory agent, or a wound-healing agent, or a skin-protective agent, or a substance intended to negate malodours, can be incorporated. Suitable antimicrobial agents include silver or silver-containing compounds, povidone iodine and substances or formulations which release hydrogen peroxide. Honey already contains an amount of glucose oxidase which acts in combination with glucose, also present in honey, to produce hydrogen peroxide. Additional amounts of glucose oxidase can be added artificially to supplement this natural activity. Suitable anaesthetics include lidocaine hydrochloride. Suitable wound-healing agents include zinc oxide.

The composite of honey-containing wound-contacting layer, intermediate layer and fabric backing layer may be produced by mixing the honey and water-absorbing agent batchwise or continuously in appropriate proportions, for example in an extruder such as a twin-screw extruder, for an appropriate period until a mixture is formed, extruding the mixture at an appropriate temperature and calendering the extruded mixture in contact with the fabric backing layer so as to achieve partial impregnation of the backing layer by the mixture. The mixing may be carried out for from 2 to 60 minutes, a mixing period of 10 minutes or more being preferred to induce some degree of set in the mixture. The mixing temperature is preferably in the range 40 to 50° C. A final heat treatment to set the honey may be desirable. At heat setting temperatures of about 80° C. setting occurs in less than 1 minute but at 50° C. setting can take up to 30 minutes.

To create a self-adhesive wound dressing, an adhesive layer may be attached to or formed integrally with the fabric backing layer. Conveniently, the adhesive layer may extend laterally outwardly beyond the periphery of the wound-contacting layer and is provided with adhesive material on such outward extension of its surface oriented towards the wound-contacting layer. The adhesive layer may thereby be caused to adhere to an area of the skin of a patent to whom the dressing is supplied surrounding a wound to be treated, while the honey layer is brought into contact with the wound. In preferred embodiments, the adhesive layer is disposed in a window-frame-type arrangement around the periphery of the fabric backing sheet, leaving at least a substantial portion of the fabric backing sheet uncovered, i.e. not overlain by the adhesive layer. This arrangement has the advantage of allowing the wound dressing to "breathe", thus permitting moisture absorbed in the honey layer to be transpired to the atmosphere.

BRIEF DESCRIPTION OF DRAWINGS

The invention will hereinafter be described in more detail, by way of example only, with reference to the accompanying drawing in which.

Figure 1:
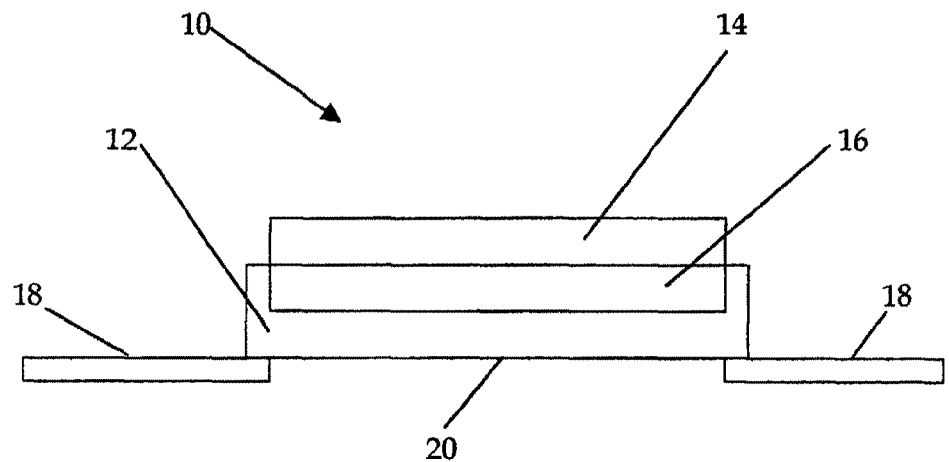
FIG. 1 is a diagrammatic representation of an embodiment of wound dressing according to the invention.

The stylised wound dressing depicted in FIG. 1 illustrates the basic structure of an embodiment of wound dressing 10 according to the invention, in which a fabric backing layer 12 is partially impregnated with a mixture of honey and sodium alginate to form an intermediate layer 16, with the remainder of the honey/alginate mixture forming a wound-contacting layer 14. A flexible adhesive fabric 18 is attached to the periphery of the underside of the fabric layer 12 and is provided on its upper surface with an adhesive substance suitable for adhering the dressing to the patient's skin. The adhesive fabric 18 is mounted to the fabric backing layer 12 in a window-frame-type arrangement, leaving a central hole 20, through which water vapour absorbed into the dressing is able to transpire.

The invention is further illustrated by reference to the following Examples

EXAMPLE 1

Figure 2:
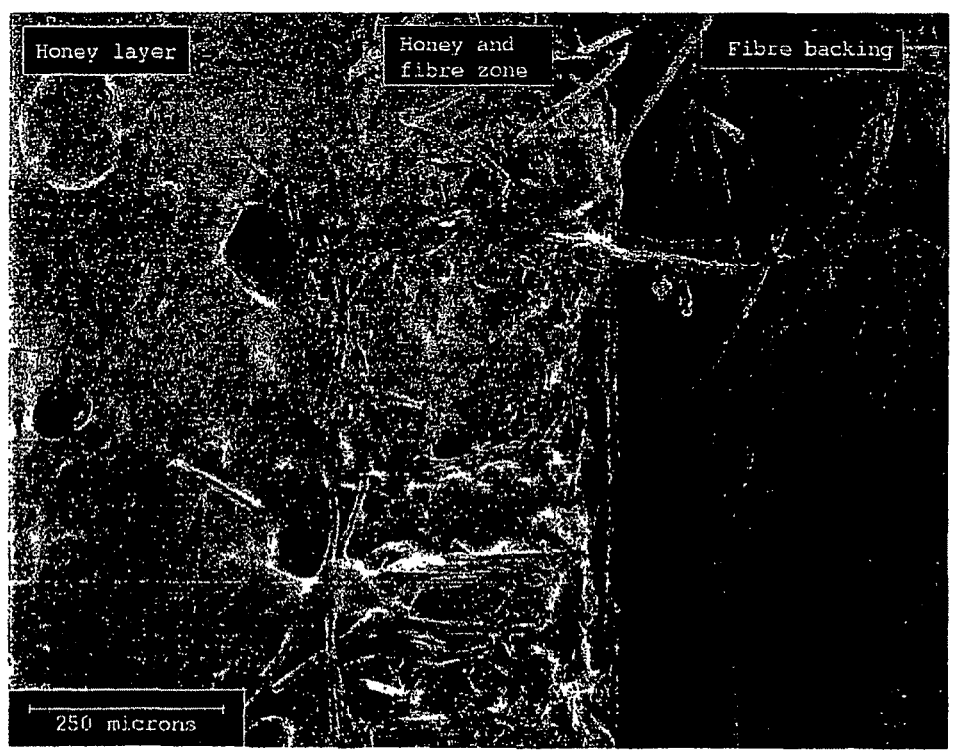
FIG. 2 is a scanning electron micrograph of a cross-section of a wound dressing manufactured according to the invention.

A test sample of a composite three-layer structure according to the invention was manufactured by the following procedure. 50 g of honey was warmed to 50° C. and added to 10 g of Keltone™ HVCR sodium alginate powder (viscosity 600-900 cP 1.25% aq. solution at 25° C. on spindle 3 of an LV Brookfield viscometer at 60 rpm). The mixture was stirred for 10 s and transferred to a petri dish. A disc of 150 gsm (gm$^{-2}$) calcium alginate fabric was placed on top of the honey/sodium alginate mixture, followed by a closely fitting support member. The assembly was then inverted and placed under pressure to spread the honey/sodium alginate mixture evenly over the fabric carrier, and heated at 50° C. for 1 hour. The assembly was then cooled and the resulting composite product removed. The sample was prepared for electron microscopy by immersion in liquid nitrogen and cut with a scalpel to produce a suitable cross-sectional surface, which was then coated with gold/palladium and analysed under a Hitachi S4000 field emission scanning electron microscope operating at 2 kV. The resulting electron microgram appears as FIG. 2 and clearly reveals a distinct three-layer structure comprising (from left to right in the figure) honey layer, honey/fibre impregnated layer, and fabric backing layer.

EXAMPLE 2

In order to test the fluid handling capabilities of dressings manufactured according to the invention, several further samples were produced, using varying ratios of sodium alginate to honey. The effect of gamma-irradiation was also studied. All of the samples were produced using 150 gsm needled calcium alginate non-woven fabric carrier and Keltone™ HVCR sodium alginate powder. The weight ratio of alginate powder to honey varied between 1:4 and 1:10. Half of the samples were gamma-irradiated (to 25 kGy) after manufacture. The samples were subjected to the Paddington Cup test, and their liquid absorbency, moisture vapour transmission rate ("MVTR"—i.e. the mass of water vapour transpired through the sample) and total fluid handling capacity ("TFHC"—i.e. the sum of MVTR and liquid absorbency) were measured in terms of grams of water per 100 cm$^2$ surface area of sample per 24 hours. The results are set out in Table 1 below:

TABLE 1

| Weight ratio of sodium alginate to honey | g/m$^2$ of sodium alginate and honey mixture in the dressing | Non-Irradiated | | | G/m$^2$ of sodium alginate and honey mixture in the dressing | Irradiated (25 kGy) | | |
|---|---|---|---|---|---|---|---|---|
| | | Absorbency | MVTR | TFHC | | Absorbency | MVTR | TFHC |
| 1:4 | 2251 | 44 | 43 | 87 | 2730 | 22 | 39 | 62 |
| | 2578 | 43 | 42 | 86 | 2401 | 29 | 39 | 68 |
| 1:4 | 4660 | 53.5 | 24.1 | 77.6 | 4090 | 35.2 | 33.7 | 68.9 |
| | 3516 | 52.8 | 33.1 | 85.9 | 3878 | 33.0 | 31.9 | 64.9 |
| 1:5 | 2259 | 40 | 45 | 85 | 2201 | 22 | 42 | 63 |
| | 2622 | 51 | 46 | 96 | 2572 | 23 | 39 | 62 |
| 1:5 | 3142 | 46.2 | 32.0 | 78.2 | 3504 | 18.7 | 36.0 | 54.7 |
| | 3258 | 48.3 | 27.4 | 75.7 | 3000 | 19.9 | 37.8 | 57.7 |
| 1:5 | 3808 | 45.9 | 30.0 | 75.9 | 3437 | 22.2 | 32.4 | 54.6 |
| | 3753 | 45.8 | 31.5 | 77.3 | 3491 | 19.7 | 36.7 | 56.4 |
| 1:5 | 3920 | 44.4 | 35.5 | 79.9 | 4153 | 19.1 | 26.5 | 45.6 |
| | 4120 | 51.2 | 30.1 | 81.3 | | | | |
| 1:10 | 3067 | 46.1 | 37.4 | 83.5 | 3154 | 12.8 | 37.6 | 50.4 |
| | 3079 | 34.6 | 33.5 | 68.1 | 3320 | 8.3 | 37.1 | 45.4 |

These results indicate that, in non-irradiated samples, all of the samples demonstrated good liquid absorbency and TFHC and that variations of alginate:honey weight ratio within the range 1:4 to 1:10 had little effect. Gamma-irradiation tended significantly to reduce liquid absorbency as the amount of honey in the alginate/honey mixture increased.

Products were made with a honey sheet having a 1:4 sodium alginate:honey ratio and with (a) 150 gsm calcium alginate needled fabric and 1350 gsm honey sheet, and (b) 70 gsm calcium alginate needled nonwoven fabric and 2500 gsm honey sheet, and these were gamma sterilized at 25 kGy. They were subsequently tested using the Paddington Cup test and, after 24 hours, showed leakage of liquid through to the back of the dressing, i.e. they were not impervious to liquid, due to the "thinness" of the product, i.e. low honey level or low fabric density.

EXAMPLE 3

To test whether the identity of the fabric carrier had any effect on fluid handling capability, four samples were produced using a 1:5 alginate:honey weight ratio, as before. Two of the samples were manufactured using 150 gsm calcium alginate needled non-woven fabric and two using Hydrocel™ (carboxymethylcellulose) 100 gsm needled non-woven fabric. Liquid absorbency, MVTR and TFHC after 24 hours were measured as previously, and the results are set out in Table 2 below:

TABLE 2

| Fabric carrier type →<br>Property ↓ | Calcium alginate | Calcium alginate | CMC | CMC |
|---|---|---|---|---|
| Weight of Honey Sheet (g/m²) | 3430 | 4190 | 4190 | 4100 |
| Nice Dome | Yes | Yes | Yes | Yes |
| 24 Hr absorbency g/100 cm² | 44.0 | 40.0 | 43.0 | 39.0 |
| 24 Hr MVTR g/100 cm² | 31.0 | 28.0 | 27.0 | 29.0 |
| 24 Hr TFHC g/100 cm² | 75.0 | 68.0 | 70.0 | 68.0 |

These results indicate that there is no significant difference between fabric carrier types or between sheet weights within the scope of the tests. The "dome" mentioned in the Table is a reference to the honey layer swollen by absorption of saline, a "nice dome" therefore being indicative, at least qualitatively, of good absorption.

EXAMPLE 4

A further test was carried out, using calcium alginate and polyester 150 gsm needlebonded non-woven fabrics, to test fluid handling over an extended period (48 hours). The results are set out in Table 3 below:

TABLE 3

| Fabric carrier type | Wt honey sheet g/m² | Absorbency g/100 cm²/ 24 hr | Absorbency g/100 cm²/ 48 hr | TFHC g/100 cm² | | MVTR g/100 cm² | |
|---|---|---|---|---|---|---|---|
| | | | | 24 hr | 48 hr | 24 hr | 48 hr |
| Alginate | 3400 | 44 | 44 | 74 | 109 | 30 | 65 |
| Polyester | 3600 | 46 | 41 | 72 | 101 | 26 | 60 |

These results demonstrate that liquid absorbency and vapour transmission rate are maintained over a period of 48 hours, there being no significant difference in absorbency between the two fabrics over that period.

EXAMPLE 5

16 kg of Manuka honey was placed into a Z-blade mixer with front and rear blades rotating at 32 rpm and 25 rpm respectively and with a circulating water jacket at 55° C. After 30 minutes, when the honey had reached a temperature of 45° C., 4 kg sodium alginate powder (Keltone™ HCVR) was added to the mixer over a 2-minute period. After a further 3.5 minutes, by which time the honey mixture was homogeneous and had reached a temperature of 48° C., the mixture was extruded through a fish-tail device by means of a screw feeder rotating at 2.5 rpm. The extruded sheet of honey mixture was 1.2 mm thick and was laid onto a support paper and then passed through calender rolls, heated to 55° C. by circulating water, with a gap set to produce the required final thickness of material. Prior to passing the extruded material through the calender rolls, 150 gsm calcium alginate needled nonwoven fabric, together with a backing release paper, was placed directly against the honey mixture. The action of the calender rolls was to achieve partial impregnation of the alginate fabric with the honey mixture. A final heat treatment, at 50° C. for 1 hour, set the honey mixture.

The above Example was repeated but this time allowing 30 minutes mixing time for the honey and powder, in order to induce a degree of set prior to extrusion. It was found that setting of the honey mixture was achieved without the need for a final heating treatment.

EXAMPLE 6

Instead of the batch operation described in Example 5, continuous mixing can be employed. A twin-screw extruder having a series of temperature zones down its length can be fed with sodium alginate powder together with downstream addition of honey at one or more injection points and mixing and heating to a series of temperature points carried out to produce a consistent mixture at a high temperature, for example of 75-80° C., so that it would start to gel immediately on extrusion, and fed to forming and calendering equipment similar to that already described in Example 5. Optimisation of the temperature profile enables the final heat treatment to set the honey mixture to be omitted.

The invention claimed is:

1. A wound dressing comprising honey and a moisture-absorbing agent, characterised in that it has a multi-layered structure comprising:
a wound-contacting layer composed of a mixture of honey and a moisture-absorbing agent that is sodium alginate, the wound-contacting layer being free from fabric;
a water-permeable fabric backing layer, the backing layer being free from honey;
and
an intermediate layer comprising water-permeable fabric impregnated with the said mixture of honey and moisture-absorbing agent,
wherein the same fabric forms the backing layer and intermediate layer and it has a weight of 100-200 gsm, and the total weight of the said mixture in the wound-contacting and intermediate layers is in the range 1500-4500 gsm, and said mixture comprises sodium alginate powder and honey in a ratio in the range 1:(2-5),
wherein the backing layer is a fabric layer that forms a continuum with the intermediate layer, and
wherein the dressing has a 24 hour moisture vapor transmission rate of at least 20 g per 100 cm² and a 24 hour total fluid handling capacity of at least 35 g per 100 cm².

2. A wound dressing according to claim 1, wherein said wound-contacting layer and said intermediate layer form a first continuous phase and said fabric layer and said intermediate layer form a second continuous phase, and said first and second continuous phases overlapping to form said intermediate layer.

3. A wound dressing according to claim 2, wherein said intermediate layer has a thickness of between 100 μm and 1,000 μm.

4. A wound dressing according to claim 3, wherein said intermediate layer has a thickness of between 200 μm and 500 μm.

5. A wound dressing according to claim 1, wherein a ratio of sodium alginate to honey is in the range of from 1:4 to 1:5.

6. A wound dressing according to claim 1, wherein the water permeable fabric backing layer is calcium alginate.

7. A wound dressing according to claim 1, further comprising,
an adhesive layer attached to or integral with said fabric backing layer, said adhesive layer extending laterally outwardly beyond the periphery of said wound-contacting layer and being provided with adhesive material on such outward extension of its surface oriented towards said wound-contacting layer to provide adhesion of said adhesive layer to an area of the skin of a patient to whom the dressing is applied, surrounding a wound to be treated.

8. A wound dressing according to claim 7, wherein at least a substantial portion of the fabric backing layer is not overlain by said adhesive layer.

9. A wound dressing according to claim 1, wherein the dressing has been gamma-irradiated.

10. A wound dressing comprising honey and a moisture-absorbing agent, characterised in that it has a multi-layered structure comprising:
- a wound-contacting layer composed of a mixture of honey and a moisture-absorbing agent that is sodium alginate, the wound-contacting layer being free from fabric;
- a water-permeable fabric backing layer, the backing layer being free from honey; and
- an intermediate layer comprising water-permeable fabric impregnated with the said mixture of honey and moisture-absorbing agent,
    - wherein the same fabric forms the backing layer and intermediate layer and it has a weight of 100-200 gsm, and the total weight of the said mixture in the wound-contacting and intermediate layers is in the range 1500-4500 gsm, and said mixture comprises a modified cellulose polymer powder and honey in a ratio in the range 1:(2-5), and
    - wherein the dressing has a 24 hour moisture vapor transmission rate of at least 20 g per 100 $cm^2$ and a 24 hour total fluid handling capacity of at least 35 g per 100 $cm^2$.

11. The wound dressing as recited in claim 10, wherein said modified cellulose polymer comprises carboxymethylcellulose.

12. The wound dressing according to claim 1, wherein the fabric is made of a non-woven fibre made from calcium alginate fabric.

13. The wound dressing according to claim 1, wherein the backing layer is a layer of fibre substantially free of honey or any other substances and the fibre in the layer is integral to the intermediate layer and is not a separate plastic cover.

14. The wound dressing according to claim 1, wherein the backing layer is constructed from a fibre that is liquid water permeable and the resulting dressing is impervious to liquid water and aqueous saline liquid.

* * * * *